United States Patent [19]

Ruoff et al.

[11] Patent Number: 4,921,293
[45] Date of Patent: May 1, 1990

[54] MULTI-FINGERED ROBOTIC HAND

[75] Inventors: Carl F. Ruoff, La Crescenta; J. Kenneth Salisbury, Jr., Palo Alto, both of Calif.

[73] Assignee: The United States of America as represented by the Administrator of the National Aeronautics and Space Administration, Washington, D.C.

[21] Appl. No.: 680,605

[22] Filed: Dec. 12, 1984

Related U.S. Application Data

[63] Continuation of Ser. No. 364,774, Apr. 2, 1982, abandoned.

[51] Int. Cl.$^5$ ............................................. B25J 15/10
[52] U.S. Cl. ..................................... 294/111; 74/479; 74/665 G; 294/106; 414/7; 414/729; 901/21; 901/36; 623/64
[58] Field of Search .................. 414/7, 729, 730, 735; 74/665 A, 665 F, 665 L, 665 G, 479, 501 M; 254/273; 116/DIG. 34, 278; 73/862.48; 294/106, 111, 86.4; 3/12.7; 901/21, 36

[56] References Cited

U.S. PATENT DOCUMENTS

| | | | |
|---|---|---|---|
| 2,819,111 | 1/1958 | Cozzens | 294/106 X |
| 3,587,872 | 6/1971 | Pauly | 414/732 |
| 3,694,021 | 9/1972 | Mullen | 294/106 |
| 3,866,966 | 2/1975 | Skinner | 3/12.7 X |
| 3,877,780 | 4/1975 | Taylor | 74/501 M X |
| 4,066,141 | 1/1978 | Elvin | 254/273 X |
| 4,218,173 | 8/1980 | Coindet | 414/732 X |
| 4,233,837 | 11/1980 | Canfield | 73/862.48 X |
| 4,246,661 | 1/1981 | Pinson | 3/12.7 |
| 4,287,759 | 9/1981 | Cooper | 73/862.48 X |

OTHER PUBLICATIONS

Kinematic and Force Analysis of Articulated Mechanical Hands, Salisbury & Roth, Journal of Mechanisms, Transmissions & Automation in Design, Mar. 1983, vol. 105.
"Articulated Hands: Force Control and Kinematic Issues", Salisbury et al, published by American Automatic Control Council, 1981.
"How Smart Robots are Becoming Smarter", Paul Kinnacan, High Technology, Sep./Oct. 1981, vol. 1, No. 1, pp. 32-40.
"A Three-Fingered, Articulated, Robotic Hand", Lian et al.
"Computer Control of Multijointed Finger System for Precise Object-Handling", Okada, IEEE Transactions on Systems, Man & Cybernetics, vol. SMC-12, No. 3, May/Jun. 1982, pp. 289-299.
Article "A Versatile End-Effector With Flexible Fingers" by Dr. Tokuji Okada, Robotics Age, Winter 1979, pp. 31-39.
Article "Design for a Three-fingered Hand" by F. R. Erskine Crossley and F. G. Umholtz, Mechanism and Machine Theory, 1977, vol. 12, pp. 85-92.
Article "Designing A Multiple Prehension Manipulator" by Frank Skinner, Mechanical Engineering, Sep. 1975, pp. 30-37.

(List continued on next page.)

Primary Examiner—Robert J. Spar
Assistant Examiner—Donald W. Underwood
Attorney, Agent, or Firm—Thomas H. Jones; John R. Manning; Charles E. B. Glenn

[57] ABSTRACT

A robotic hand having a plurality of fingers, each having a plurality of joints pivotally connected one to the other, with actuators connected at one end to an actuating and control mechanism mounted remotely from the hand and at the other end to the joints of the fingers for manipulating the fingers and passing externally of the robot manipulating arm in between the hand and the actuating and control mechanism. The fingers include pulleys to route the actuators within the fingers. Cable tension sensing structure mounted on a portion of the hand are disclosed, as is the covering of the tip of each finger with a resilient and pliable friction enhancing surface.

9 Claims, 3 Drawing Sheets

OTHER PUBLICATIONS

Paper "Artificial Hand Mechanisms" by D. S. Childress, contributed by the Design Engineering Division of the American Society of Mechanical Engineers for presentation at the Mechanism Conf. & Int'l Symposium on Gearing and Transmissions, San Francisco, CA, Oct. 1972.

Paper, "Precision Insertion Control Robot and Its Application" by K. Takeyasu, T. Goto and T. Inoyama, contributed by the Mechanisms Committee of the Design Engineering Division for presentation at the Design Engr. Technical Conference, Montreal, Canada, Sep. 26–29, 1976, of the American Society of Mechanical Engineers, Manuscript received at ASME Hqtrs. 6/23/76, Paper No. 76-DET-50.

Paper "Synthesis and Control of the Anthropomorphic Two-Handed Manipulator" by A. Morecki, Z. Busko, H. Gasztold and K. Jaworek, work done at the Group of Technical Biomechanics, Institute of Aeronautical Engineering and Applied Mechanics, Technical University of Warsaw, Poland.

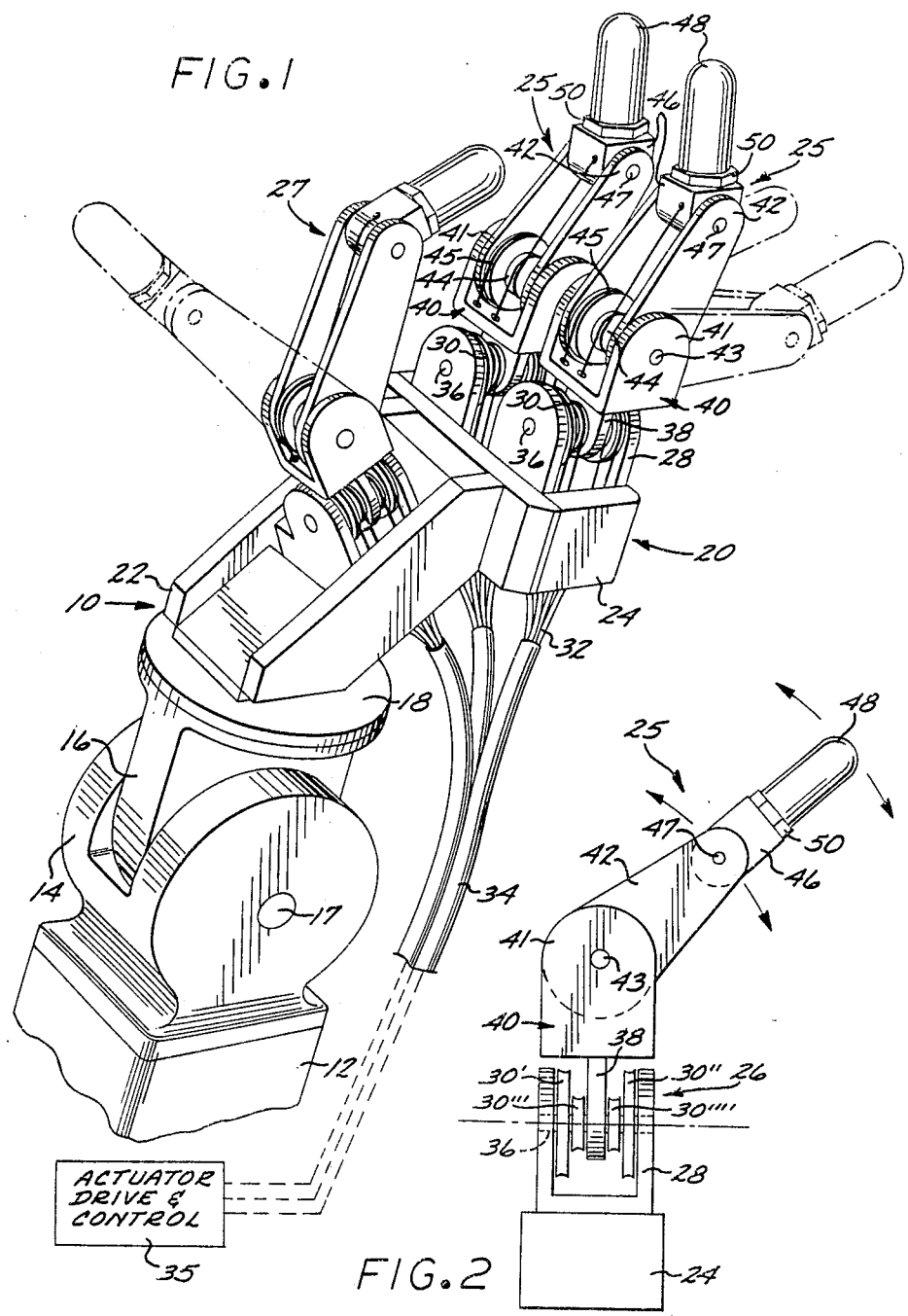

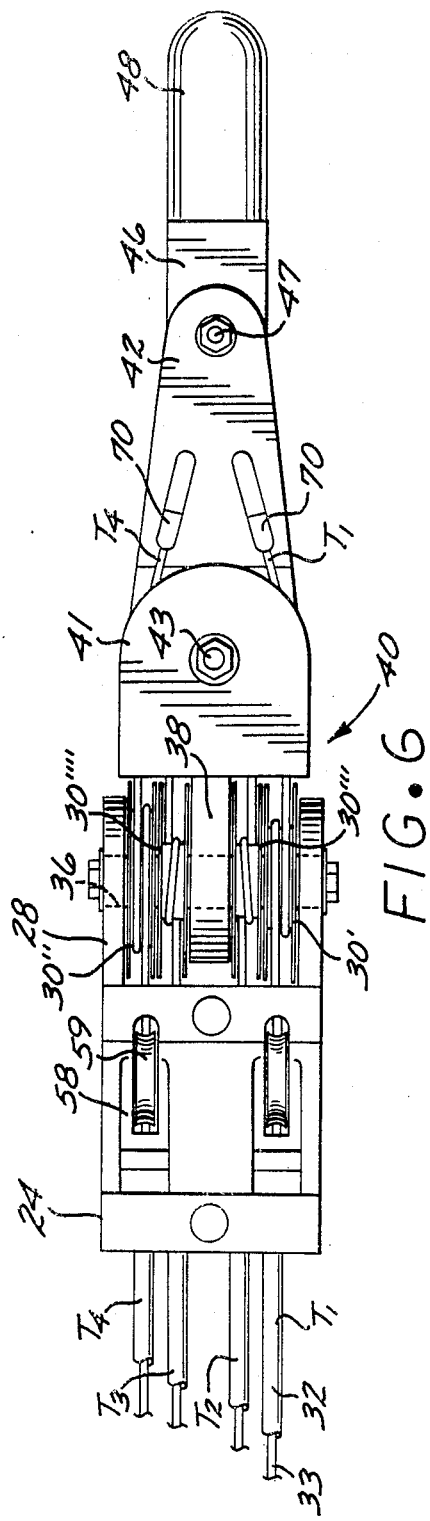
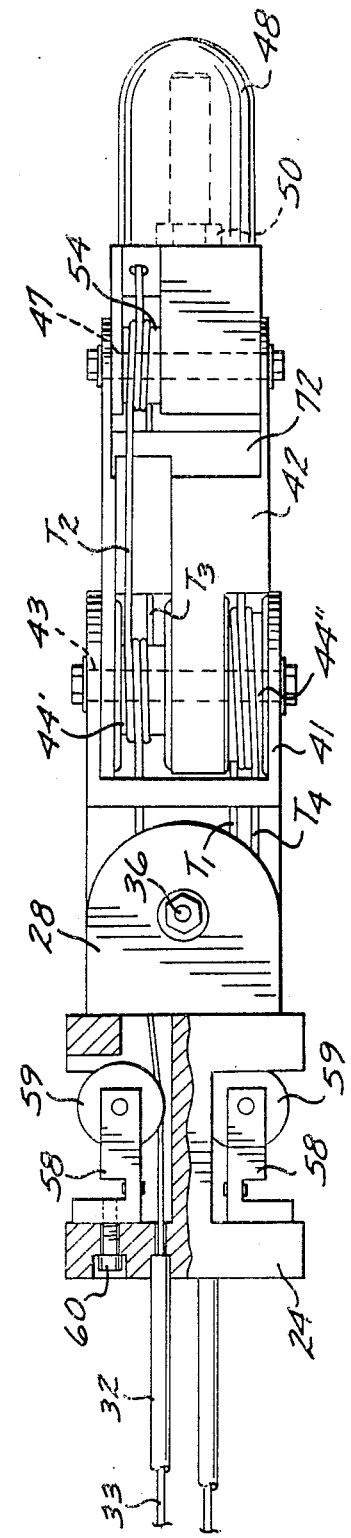

MULTI-FINGERED ROBOTIC HAND

This application is a continuation of application Ser. No. 364,774, filed Apr. 2, 1983, now abandoned.

FIELD OF THE INVENTION

The present invention relates to robot manipulators having end effectors, i.e. robotic hands.

BACKGROUND AND SUMMARY OF THE INVENTION

In the past robotic manipulators have generally employed a six-degrees-of-freedom arm with an end effector, i.e. hand, capable of only simple grasping. Typically such end effectors used in the past have included two vise-like clamping fingers having together only one-degree-of-freedom of movement, due to being coupled together for movement purposes. Two problems that exist with such end effectors are that they are (1) unable to adapt to a wide range of object shapes; and (2) unable to make small displacements at the hand without moving the entire manipulating arm. This limits the response and fidelity of force control to that of the entire manipulator arm, even for very small motions. For example, often the most critical and necessarily accurate motions in a robot-controlled assembly task are of a very small magnitude in comparison to the range of motion of the entire arm. For example, once the manipulator has placed an object to be assembled in contact with another object, the motion necessary to complete the assembly may be less than one centimeter with an angular movement of less than 20 degrees. To make such motions it is necessary to very finely control the joints of the arm itself, which joints are typically designed to move through working volumes of one-half meter in radius or more.

One solution of this problem has been an attempt to use robot manipulators having actuators for the hands located on the forearm of the manipulator. Such actuators have been connected to the fingers by bare cables passing over a plurality of pulley sheaves in the manner of vintage dentist's drills. The wrists of such robot arms are complicated gimbaled affairs requiring more than one gimbal per cable. Consequently, the number of fingers and the degrees of freedom of each finger are severely limited by the complexity and crowding with the wrist mechanism. This limits the capability of such end effectors, i.e. hands, and makes them slow and cumbersome to manipulate and control, comparing quite poorly with actual human hand. Further, the weight and inertia of such hands require that they be specially designed together with the arm on which they are to be mounted and with painstaking attention having to be paid to the effects on their control parameters.

Another solution to the problem has been the attempted use of small motion-producing devices between the end effector and manipulator arm. The remote center compliance device discussed in Drake, "Using Compliance in Lieu of Sensory Feedback for Automatic Assembly," Charles Stark Draper Laboratory Report T-657, September 1977, is an example of a passive approach to such motion-producing devices between the end effector and the arm. A three-axis force-controlled assembler developed by Hill at SRI is an example of an active small motion device. However, both of these attempted solutions used end effectors suitable only for static grasping rather than combining the moving and grasping functions. This approach limits manipulative ability by (1) the lack of a stable adaptive grasp necessitating tool changes or limiting the class of manipulatable objects; and (2) placing the mass of the gripper and its actuator after the small motion device, thereby imposing a lower bandwidth on motion of the manipulator and end effectors at a given power. In addition, since these were capable only of grasping, the manipulative function was carried out for the most part by the manipulative arm itself.

Numerous designs have been presented for multifinger hands suited for grasping only. Some examples of these are shown in Skinner, "Designing a Multiple Prehension Manipulator," Mechanical Engineering, September 1975; Crossley & Umholtz, "Design for a Three Fingered Hand," Mechanism and Machine Theory, Vol 12, 1977; Childress, "Artificial Hand Mechanisms," Mechanisms Conference and International Symposium on Gearing and Transmissions, San Francisco, California, October 1972; Rovetta, "On Specific Problems of Design of Multi-Purpose Mechanical Hands in Industrial Robots," Proceedings 7 ISIR, Tokyo, 1977. Such designs have generally been aimed at approximating a subset of human grasping patterns observed to be useful in human functions.

A three-fingered design with a total of 11 degrees of freedom has been described in Okada, "Computer Control of Multi-Jointed Finger System," Sixth International Joint Conference on Artificial Intelligence, Tokyo, Japan, 1979. Okada uses a heuristic combination of position and force control fingers to grasp objects and impart some limited motion. While it is capable of some independent small motions, in an anthropomorphic manner, the Okada device requires a special arm design to accommodate it and a special control system. The Okada device does not address the problem of general motion of grasped objects.

The Okada apparatus has two cables per degree of freedom, i.e. joint for a total of 22 cables, all of which were passed through wrist gimbals. The arm is therefore severely limited and massive in size. In particular, the bare cables passing through the wrist joint cause a high degree of mechanical complexity and limited wrist motion. Moreki, "Synthesis and Control of Anthropomorphic Two-Handed Manipulator," Proceedings of the Tenth International Symposium on Industrial Robots, Milan, Italy, 1980 discloses that the number of control cables for each end effector, i.e., hand, can be significantly reduced. Moreki showed that for n degrees of freedom, n+1 cables can be used, and separate cable tensioning would not be needed.

One of the co-inventors of the present invention has pointed out, as co-author of a paper, Salisbury & Craig, "Articulated Hands: Force Control and Kinematic Issues," Proceedings of the 1981 Joint Automatic Control Conference, Charlottesville, Virginia, 1981, that contact by as few as seven frictionless points can immobilize a wide range of objects, i.e. grasp them securely against falling in any direction. However, the resulting implementation and design problems are formidable. In addition, an object held this way could not be rotated against resistance if it were a surface of revolution, e.g. a door knob or a cylindrical handle.

It is therefore quite desirable to have an end effector, i.e. hand, with a reasonable number of degrees of freedom and which has its actuators mounted, e.g. on the more massive forearm of the manipulating arm. It is also quite desirable to eliminate passage of the actuator's cables operatively through the mechanism of the wrist, thereby limiting the complexity of the wrist and avoiding multiple wrist gimbals. Such a hand would have the advantage of being transferrable from arm to arm if properly designed to be adapted to fit at the end of different arms, and would thereby be universal in its applicability. Such a hand would also improve present performance of robot manipulators, while reducing costs and enhancing the commercial applicability of robot manipulators.

The problems enumerated in the foregoing are not intended to be exhaustive, but rather are among many which tend to impair the effectiveness of previously known robot manipulating arms and end effectors. Other noteworthy problems may also exist; however, those presented above should be sufficient to demonstrate that robot manipulator arms having end effectors appearing in the art have not been altogether satisfactory. Recognizing the need for an improved end effector for a robot manipulating arm, it is, therefore, a general purpose of the present invention of providing a novel end effector which minimizes or reduces the problems of the type previously noted. A feature of the present invention employs using sheathed actuator cables which are operatively routed entirely outside the wrist gimbals enabling the hand to be used on a wide range of robot manipulator arms with only minor adaptations and to be universally mountable on a wide variety of manipulator arms. An additional feature of the present invention is to employ a plurality of, e.g. three fingers, having, e.g. three joints each. Still another feature, which may be employed with the present invention, is to employ frictional contact areas at the tips of each of the fingers to facilitate rotating all gripped objects, including those having surfaces of revolution, and reduce the necessary number of contact points for firmly grasping the object to be gripped. For example, three fingers, especially with friction contact, can easily grasp and rotate a sphere and a wide variety of other object shapes, because of the wide range of permitted grip positions. It is a further feature of the present invention to provide a robotic hand which can accomplish a wide range of rapid, small and precise motions on a wide range of objects sizes and shapes without the need of involving the remainder of the manipulator arm. The further feature of the present invention is to provide sheathed cables from the cable drive motors mounted remotely on the, e.g. forearm of the manipulator arm, which eliminates the need for routing pulleys, except in the joints in the end effector itself.

A further feature of the present invention is to obtain force and torque data by measuring the strain on the support structure, for example, those carrying the pulley sheaves over which the cables pass in, e.g. the palm of the hand.

Examples of the the more important features of the present invention thus have been summarized rather broadly in order that the detailed description thereof that follows may be better understood, and in order that the contribution to the art may be better appreciated. There are, of course, additional features of the invention that will be described hereinafter and which also form the subject of the appended claims. Other features and advantages of the present invention will become apparent with reference to the following detailed description of a preferred embodiment thereof, in connection with the accompanying drawings, wherein like reference numerals have been applied to like elements, in which:

BRIEF DESCRIPTION OF THE DRAWINGS

FIG. 1 depicts a perspective view of a robot manipulator end effector, i.e. hand, according to the present invention;

FIG. 2 is a side view of a multi-jointed end effector finger according to the present invention;

FIGS. 6 and 7 show respectively plan and side views of a further embodiment of the finger.

DETAILED DESCRIPTION OF A PREFERRED EMBODIMENT OF THE INVENTION

Figure 3:
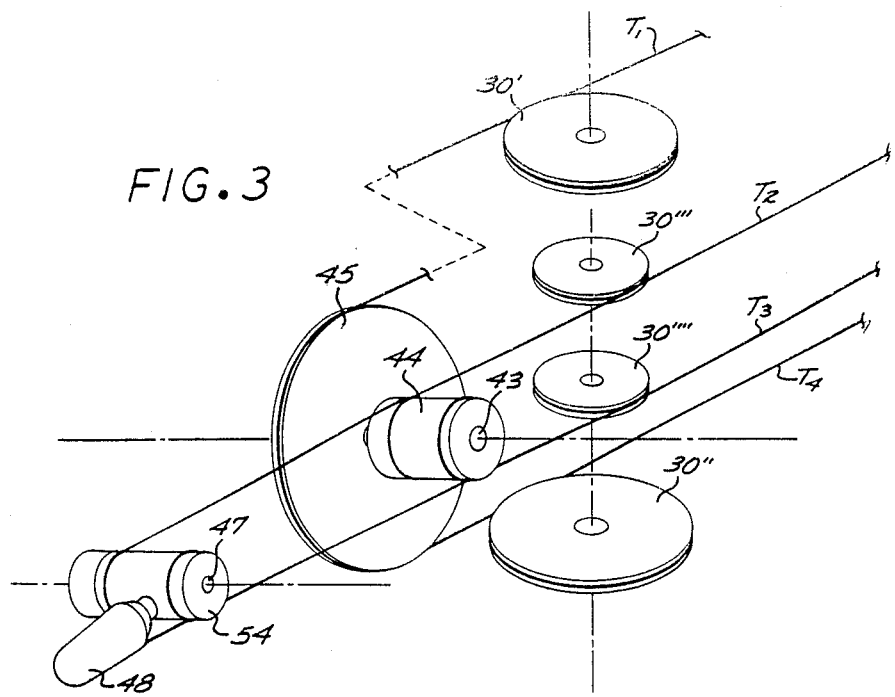
FIG. 3 is an exploded schematic view of the actuator cable and pulley system for each of the multi-jointed end effector fingers of the hand according to the present invention.

Turning now to FIG. 1, a perspective view is shown of the robot manipulator having a multiple-fingered end effector, i.e. hand 10, in which each finger is multiple-jointed in accordance with the present invention. The hand 10 is attached to the terminal end of a robot manipulator arm 12 by an end bracket 14 in which a wrist joint 16 is pivotably mounted on pin 17. The wrist joint 16 has a wrist plate 18 which is mounted on the wrist joint 16 for rotating about an axis perpendicular to the axis pin 17, thereby giving the wrist assembly itself, including the wrist joint 16 and wrist plate 18, two degrees of freedom of movement.

Attached to the wrist plate 18 is a robotic hand palm member 20 which contains an angular member 22 affixed to the wrist plate 18 and a terminal member 24 affixed to the opposite end of the angular member 22.

The robotic hand 10 forming the end effector of the robotic arm 12 as shown in FIG. 1 contains two fingers 25 and a thumb 27, with the thumb 27 mounted on the angular member 22 and the two fingers mounted on the terminal member 24. Each of the fingers 25 and the thumb 27 is identical in structure (it being understood that they might not necessarily be identical in size) and includes a first joint 26. A pulley sheave bracket 28 is mounted on the respective portion 22, 24 of the palm member 20. Contained on the pulley sheave bracket 28 are four pulleys 30, mounted for rotation about a pin 36 through the two sides of the pulley sheave bracket 28, as is described in further detail with respect to FIG. 2. Four sheathed cables 32 for each of the fingers 25 and thumb 27 enter into openings (not shown in FIG. 1) in the palm 20 structure, as explained more fully below. Each group of four sheathed cables 32 for each finger 25 or thumb 27 is bundled together in a bundling sleeve 34 for convenient containment and guidance between the motor actuators in an actuator drive and control mechanism 35, shown schematically in FIG. 1, which is mounted remotely from the hand 10, e.g. on the forearm of the manipulator arm 12.

Also mounted for rotational movement about pin 36 is a pivotable attachment 38 for a first joint 40, which includes a second joint bracket 41 attached to the pivotable attachment 38. The second joint bracket 41 has mounted thereon, for pivotable rotation about a pin 43, a second joint 42 and an idler pulley 44. The second joint 42 has affixed thereto a second joint drive pulley 45, also mounted for rotation on pin 43. The second joint 42 has mounted thereon at its other end, for pivotable rotation about a pin 47, a third joint bracket 46 onto which is mounted a third joint 48 which is fixed to the third joint bracket 46 by a nut 50. The third joint as shown in FIG. 1 is covered with a resilient material, having a surface which serves to frictionally engage objects to be grasped by the hand 10. This material could be, e.g. a hard rubber compound which exhibits the desired properties of some flexibility and compliability while being also somewhat firm and durable, thus being able to facilitate grasping oddly shaped objects in the manner of human fingers and having an acceptable durable life. It will be seen from FIG. 1 that the two fingers 25 may incline towards each other by rotation of the first joint 40 on pin 36. However, they do not oppose one another as the thumb 27 opposes the fingers 25, as it is spaced spart from them in a line perpendicular to the axes of pins 41 and 45 on the finger 25. FIG. 1 shows the hand in the act of grasping on object, e.g. a sphere (not shown) with the phantom positions of the fingers 25 and thumb 27 illustrating the hand 10 in an open position prior to movement of the fingers 25 and thumb 27 into the grasping position.

Turning now to FIG. 2, there is illustrated the construction of one of the fingers 25 or the thumb 27 in a side view, taking, for example, one of the fingers 25 mounted on the palm 20 terminal member 24. It can be seen that the tip 48 rotates about an Axis 3 through pin 47 and the second joint 42 rotates in the same plane around an Axis 2 through pin 43. Axis 1, through pin 36, about which the first joint 40 rotates, is in a plane perpendicular to that of the two Axes 2 and 3, with the first joint 40 rotating in and out of the paper as shown in FIG. 2.

In FIG. 3 the cable and pulley system of the fingers 25 or thumb 27 is shown partially schematically and in a perspective exploded view. The tip joint 48 is moved by two cables $T_2$ and $T_3$, the ends of both of which are wrapped around a tip joint idler pulley 54, rotatably mounted on pin 47, and are attached to the tip joint 48, although only one such attachment can be seen in FIG. 3. It will be understood that one cable could be employed to form $T_2$ and $T_3$ and also that the cable or cables could be attached to the idler pulley instead of to the tip 48, in order to assist in ensuring the rotation of the tip joint 48 without any cable slippage on the idler pulley 54. Each of the cables $T_2$, $T_3$ is also wrapped about the idler pulley 44 on Axis 2, which has a radius of $R_2$, equivalent to the radius of the idler pulley 54, although such equivalency in radius is not necessary to the operation of the fingers of the present invention. It will also be understood that the idler pulley 44 on Axis 2 could actually be two separate idler pulleys, one for each of the cables $T_2$ and $T_3$. Each of the cables $T_2$ and $T_3$ passes around one of the pulley sheaves 30 on Axis 1, respectively 30''' and 30'''', which are also of radius $R_2$, this again being optional. The pulley sheaves 30''' and 30'''' are shown in the exploded view to be slightly larger, in order to illustrate the orthogonally tangential relationship between the exist point of the respective cables $T_2$ and $T_3$ from the respective pulleys 30''' and 30'''' and the point of initial contact with the idler pulley 44 by each of the cables $T_2$ and $T_3$.

It will be seen that by applying tension to cable $T_2$ the tip joint 48 will be rotated in a direction towards the top of FIG. 3, and will also apply tension on cable $T_3$ so that it unwinds from its motor capstan (not shown) mounted, for example, on the forearm of the robotic manipulator arm 12, included within the actuator drive and control mechanism 35. Axes 1 and 2 will rotate slightly as well. Conversely, applying tension to cable $T_3$ will rotate the tip joint 48 in a downward direction as shown in FIG. 3, unwinding cable $T_2$ in a similar manner as described for cable $T_3$ and causing Axes 1 and 2 to rotate in the opposite direction. Cables $T_1$ and $T_4$ are in reality a single cable which passes around pulley sheave 30' on Axis 1 and second joint drive pulley sheave 45 on Axis 2 and then around pulley sheave 30'' again on Axis 1. The pulley sheaves 30', 30'', and 45 have a radius $R_1$ which is larger than radius $R_2$, however, the pulley sheave 45 is shown in FIG. 3 to actually have a radius $R_3$ larger than $R_1$, in order to illustrate the tangential relationship of the cable alignment from pulley sheaves 30' and 30'' in the exploded view. The pulley sheave 45 is fixedly attached to the second joint 42 such that applying tension on the cable $T_1$ will rotate the second joint 42 in a clockwise direction as shown in FIG. 3, and the application of tension on cable $T_4$ will rotate the pulley 45 and second joint 42 in a counterclockwise direction, causing the second joint 42 to move in a direction corresponding to downward, as shown in FIG. 3. It will be understood that pulley 45 could be an idler pulley, with the terminal ends of cables $T_1$ and $T_4$ affixed to the second joint 42 in order to effect rotation thereof by the application of tension on either cable $T_1$ or $T_4$.

In order to mount all four pulley sheaves 30', 30'', 30''', 30'''' contiguously on Axis 1, i.e. pin 36, and to make the 90-degree turn to idler pulley 44 and pulley sheave 45 on Axis 2, the respective pulleys 30''', 30'''' and 44 and 30', 30'' and 45 at the adjacent Axes 1 and 2 should be tangent to each other and matched in radius. Two sizes of pulleys 30 are used in order to pass four cables through the pivotable connection of the first joint 40 and second joint 42. In FIG. 3 the three different radii $R_1$, $R_2$ and $R_3$ are employed to illustrate in the exploded view the tangential relationship. Those skilled in the art will appreciate that various cable routing and guiding techniques could be employed, and that FIG. 3 is intended to be a schematic illustration of one such guiding and routing technique. A slightly different one is shown in FIGS. 6 and 7, from that shown in FIGS. 1 or 3. One skilled in the art would appreciate the variations possible on the pulley diameter relationship and cable rigging used, and the various design tradeoffs in selecting an appropriate pulley and cable rigging design.

There is no direct cable connection to the base joint 40 at Axis 1. However, it can be moved by pulling on the proper pair of cables $T_1$-$T_4$ or $T_2$-$T_3$ together. Thus, if cables $T_2$ and $T_3$ simultaneously have tension applied to them, cables $T_1$ and $T_4$ will pay out, but there will be no relative motion of this cable pair. However, since both $T_2$ and $T_3$ pass into and away from the pulley sheaves 30''' and 30'''' on Axis 1 on the same side, there will be a torque exerted on the base, i.e. first joint 40, which will pivot the base joint 40 in a counterclockwise direction about Axis 1 as viewed from the perspective of FIG. 3. Similarly, applying tension to both cables $T_1$ and $T_4$ will have the opposite effect of rotating the base joint 40 about pin 36 in a clockwise direction as viewed from the perspective of FIG. 3.

The equations for motion of each of the respective first-third joints of each of the fingers or thumb 25, 27 are as follows for the illustration of FIG. 3:

$$\text{Torque}_1 = -T_1 R_1 + T_2 R_2 + T_3 R_2 - T_4 R_1$$

$$\text{Torque}_2 = T_1R_3 + T_2R_2 - T_3R_2 - T_4R_3$$

$$\text{Torque}_3 = T_2R_2 - T_3R_2$$

It will, of course, be appreciated that these relations depend upon the actual pulley sizes selected for routing the various cables $T_1$ through $T_4$, which may in some designs all be slightly different, thus inserting four different radii to these equations $R_1$-$R_4$.

Figure 5:
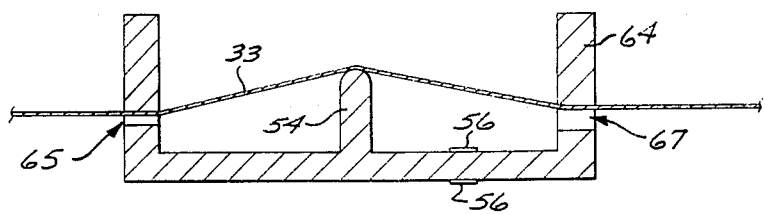
FIG. 5 shows an alternative embodiment of a cable tension sensor according to the present invention.

FIG. 5 shows one embodiment of a cable strain measuring gauge according to the present invention. Shown in cross-section is a strain measuring deflecting member 64 which is placed on the cable 33 within the terminal member 24. The unsheathed cable 33 enters an opening 65 in the wall of the deflecting member 64. Attached to the side wall of the deflecting member 64 is a central strut 54 over which the cable 33 passes prior to exiting through a second opening 67 in an opposing wall of the deflecting member 64. Strain gauges 56 are placed on the wall of the deflecting member 64 between the central strut 54 and the exit opening 67 and measure the strain on the deflecting member 64, which is a function of the tension on the cable 33.

Figure 4:
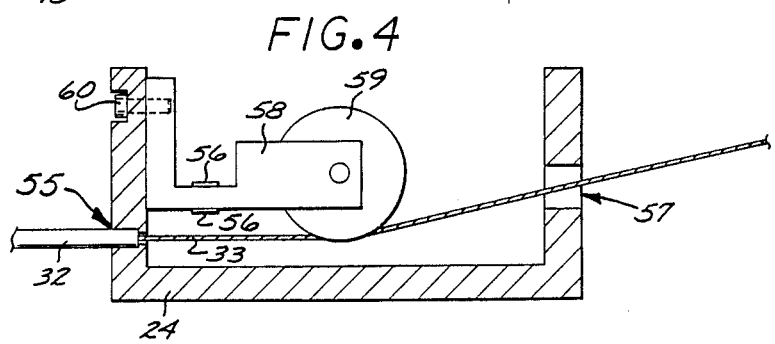
FIG. 4 shows an embodiment of a cable tension sensor according to the present invention.

FIG. 4 shows an alternative embodiment having a pulley sheave 59 which cannot be seen in the perspective view of FIG. 1, but can be seen in FIGS. 6 and 7. Attached to an interior portion of the terminal member 24 is a cantilever mounting 58, for example, by the cantilever mounting 58 being screwed on the interior surface of the wall of the terminal member 24 by screw 60. The pulley sheave 59 is rotatably mounted on the cantilever 58. In this embodiment the strain gauges 56 are placed on the cantilever mounting 58 and measure the strain on the cantilever mounting 58 created by the cable 53 passing over the pulley sheave 59, which is also a function of the tension on cable 33. A strain gauge according to the embodiments of FIGS. 4 or 5 is contained within the palm 20 structure for each cable $T_1$-$T_4$ for each finger 25 and thumb 27.

Any of a number of control systems 35 well known in the art can be used to handle the strain gauge matrix calculations employing the strains as measured as shown in FIGS. 4 and 5 for each of the four cables $T_1$ through $T_4$. One such possible control system is discussed in the above-mentioned paper of Salisbury, a co-inventor of the present invention, and Craig, the disclosure which is hereby incorporated by reference. The control system 35, which may be mounted, e.g. on the forearm of the manipulator arm 12, handles the calculations and provides outputs to drive motors. The drive motors may employ, e.g. conventional incremental shaft position encoders to obtain position, velocity and acceleration data for the drive motors to which the cables $T_1$ through $T_4$ are attached, having been passed thereto in the cable bundling sleeve 34, such that the individual joint torques and forces yield the desired total and combined grasping and twisting parameters for the hand.

Turning now to FIGS. 6 and 7, there is shown, first in FIG. 6, a side view similar to that of FIG. 2 of a finger 25 mounted in the terminal portion 24 of the palm member 20, in further detail than FIG. 2 and with a slightly different cable rigging than is shown in FIG. 1, and in FIG. 7, a plan view of FIG. 6, with the finger 25 rotated 90 degrees out of the paper from the view shown in FIG. 6. FIG. 6 shows the sheathed cables 32, $T_1$ through $T_4$ entering the terminal portion 24 of the palm member 20 and each passing, unsheathed, over a tension sensor apparatus pulley 59 mounted on a cantilever mounting 58.

Each of the unsheathed cables 33 passes over its respective pulley 30' through 30'''' on pin 36. Cables $T_2$ and $T_3$ pass over the centrally mounted pulley sheaves 30'' and 30''' respectively, each having the same radius. As can be seen in FIG. 7, this identity of radius is used because the cables $T_2$ and $T_3$ are wrapped in a double helical fashion over one idler pulley 44' on the axis about pin 43, and because of the distance between cables $T_2$ and $T_3$ as they exit their respective pulleys 30'' and 30'''. Cables $T_1$ and $T_4$ each pass over their respective pulley 30' and 30'''' and on to a second idler pulley 44'' on pin 36. The radius of pulley 44' is greater than that of pulley 30'', which is in turn greater than that of pulley 30'. This relation between the radius of pulleys 30' and 30'' results from the side-by-side wrapping of cables $T_1$ and $T_4$ on pulley 44'', as shown in FIG. 7, which requires, for preserving tangential relationships, that pulley 30' be slightly smaller than pulley 30''. The ends of cables $T_1$ and $T_4$ are connected to joint 42 by fasteners 70 on opposite sides of the longitudinal axis of joint 42 as seen in FIG. 6. It will be seen that each joint has faired portions to simulate the shape of a human finger with cable passages cut out of the fairings to enable cable passage as necessary. Also there are provided curved bearing surfaces, e.g. 72 to provide a smooth bearing surface should a cable contact the joint fairings during movement of the joint.

SUMMARY OF THE ADVANTAGES AND SCOPE OF THE INVENTION

With the hand, according to the present invention, mounted on, for example, a PUMA arm having the drive packages located on the forearm, there is little effect on the response bandwidth during the finger actuation. This is so since the weight and inertia of the actuators are no longer loads on the hands actuators, and are easily accommodated on the larger forearm, and have a much smaller effect on the response of the forearm. The actuating cables do not run through wrist joint gimbals, but rather run in bundles alongside the arm and the wrist. Each cable has its own sheath and several cables are bundled together for strength and placed inside a bundling sleeve for protection. Thus, the hand itself gives a total of 9 degrees of freedom of movement, with only 12 cables and no extra cable tensioning devices, which very favorably compares with the prior art Okada apparatus employing 22 cables (with only 9 degrees of freedom of movement Okada would need 18 cables), and necessitating cable passage through the wrist joint. It will be appreciated that the cables and/or cable bundles could be passed through the wrist area, if possible, desirable and useful for reducing fouling problems. However, these cables and/or bundles need not be so passed on gimbals, using, e.g. pulley arrangements in the wrist. The hand cables can be totally free of any operative connection within the wrist mechanism of the manipulator arm. In this sense the cables pass externally of the manipulating arm and its wrist mechanism. It will also be noted that the hand according to the present invention, like the human hand, can provide more than three contact areas, since more than one joint per finger can contact the object to be grasped. Also like the human hand, the object can be moved about, twisted, rotated, etc. for a wide variety of tasks by finger motion alone. The frictional surface on the tip joints further facilitates such action by the hand. The hand can be used as a prosthetic device, in which event its anthropomorphic actions would yield a far more satisfactory result for the user than the present claw-like appendages, replete with hooks, etc. As a robot hand, the hand is far superior to those of the prior art in terms of degrees of freedom of movement of the hand in conjunction with the simplicity and ease with which the hand of the present invention can be manipulated to grasp, twist, rotate, etc. various sizes and shapes of objects.

The foregoing description of the invention has been directed to a particular preferred embodiment in accordance with the requirements of the Patent Statutes and for purposes of illustration. It will be apparent, however, to those skilled in the art that many modifications and changes in both apparatus and method may be made without departing from the true scope and spirit of the invention. For example, the hand could have more than three fingers, and some or all of the fingers could have more than three joints. Of course, less than three fingers and/or joints could also be used. Further, the actuating cables might be entirely unsheathed and/or unbundled, the sheaths and bundles being added for convenience and simplicity of the cable rigging and to keep the cables clean in their passage from the actuator control and drive mechanism to the hand. Any suitable cable tensioning apparatus and control system could be used and mounted in any suitable way in a desired location remotely from the hand, including a location off of the manipulator arm, though mounting in the forearm of the manipulator arm appears to be the most convenient location for several reasons, e.g. a shortened cable length from actuator mechanism to the hand, and also a reduced likelihood of the cables fouling on the manipulator arm as it moves. Also the hand could be used without a wrist joint, and attached fixedly to a wristless manipulator arm. Also, the mountings for the first joint mounting brackets could be canted slightly towards each other and/or the thumb, with a resulting intersection of Axis 1 of each of the fingers, so that rotation of both finger second and third joints would tend to bring the respective tips together at a point, even without rotation of the two fingers at the first joint. These and other modifications within the skill of the art will be apparent to and appreciated by those of skill in the art. Applicants intend in the following claims to cover all such equivalent modifications and variations as fall within the true scope and spirit of the invention.

What is claimed is:

1. Apparatus adapted for use in a mechanical hand comprising:
    a first finger joint pivotally connected to said hand;
    a second finger joint pivotally connected to said first finger joint;
    a third finger joint pivotally connected to said second finger joint;
    first, second, third and fourth control cables; and
    means for guiding and attaching said first, second, third and fourth control cables with respect to said first, second and third finger joints such that pulling the second and third cables in opposite directions while holding the first and fourth cables fixed rotates the third joint, such that holding said second and third cables fixed while pulling the first and fourth cables oppositely to one another rotates the second joint, and such that pulling the second and third cables in the same direction, while permitting the first and fourth cables to move, rotates the first joint in a first direction and pulling the first and fourth cables, while permitting the second and third cables to move, rotates the first joint in a direction opposite to said first direction.

2. In a mechanical hand having an articulated finger with a first joint positioned along a first axis and a second joint positioned along a second axis with the second joint positioned outboard of the first joint, the improvement comprising:
    a first idler pulley positioned along said first axis;
    a first drive pulley positioned along said second axis with rotational movement of the first drive pulley causing articulation of the finger at said second joint;
    a first cable drive engaging said first idler pulley and said first drive pulley;
    said first cable drive producing rotation of said first idler pulley and said first drive pulley, and
    means to fix the position of said first idler pulley such that movement of the first cable drive produces articulation of the finger at said first joint.

3. The mechanical hand of claim 2 including:
    a second idler pulley positioned along said first axis;
    a second cable drive engaging said second idler pulley, and
    means to fix the position of said second idler pulley,
    whereby movement of the second cable drive with the position of the second idler pulley fixed produces articulation of the finger at said first joint in a direction opposite to the articulation of the finger at said first joint which is provided by fixing the position of said first idler pulley and applying movement of the first cable drive to the first idler pulley.

4. The mechanical hand of claim 3 wherein,
    said first cable drive drivingly engages said first idler pulley at a first position;
    said second cable drive drivingly engages said second idler pulley at a second position, and
    said first and second positions are on opposite sides of said first axis.

5. The mechanical hand of claim 3 including:
    a third joint positioned along a third axis;
    said third joint positioned outboard of said second joint;
    a second drive pulley positioned along said third axis with rotation of said second drive pulley producing articulation of the finger at said third joint, and
    said second cable drive engaging said second drive pulley.

6. The mechanical hand of claim 2 wherein
    said second axis is perpendicular to said first axis.

7. The mechanical hand of claim 5 wherein
    said second and third axes are each perpendicular to said first axis.

8. The mechanical hand of claim 2 wherein
    said first cable drive has two ends, and
    pulling on both of the ends of said first cable drive fixes the position of said first idler pulley.

9. The mechanical hand of claim 3 wherein
    said second cable drive has two ends, and
    pulling on both of the ends of said second cable drive fixes the position of said second idler pulley.

* * * * *